US00PP10236P

United States Patent [19]

Wain

[11] Patent Number: Plant 10,236

[45] Date of Patent: Feb. 10, 1998

[54] CHRYSANTHEMUM PLANT NAMED 'BRIGHT YELLOW FIJI'

[75] Inventor: Peter Wain, Hayling Island, United Kingdom

[73] Assignee: Cleangro Ltd., Chichester, United Kingdom

[21] Appl. No.: 648,927

[22] Filed: May 16, 1996

[51] Int. Cl.[6] ..... A01H 5/00

[52] U.S. Cl. ..... Plt./78

[58] Field of Search ..... Plt./78

*Primary Examiner*—Howard J. Locker

*Attorney, Agent, or Firm*—C. A. Whealy

[57] ABSTRACT

A distinct cultivar of Chrysanthemum plant named Bright Yellow Fiji, characterized by its flat capitulum form; decorative-type inflorescences; early flowering; bright yellow ray florets; numerous inflorescences per plant when grown as a spray; numerous ray florets per inflorescence; strong stems; and strong and long peduncles.

1 Drawing Sheet

The present invention relates to a new and distinct cultivar of Chrysanthemum plant, botanically known as *Dendranthema grandiflora* and referred to by the cultivar name Bright Yellow Fiji.

The new cultivar is a spontaneous mutation of the commercial cultivar Fiji (U.S. Plant Patent application Ser. No. 08/648,930). The new cultivar was discovered and selected in May, 1992, by the inventor in a controlled environment in Havant, Hampshire, United Kingdom, as a single plant among a population of plants of the cultivar Fiji. This single plant consistently formed inflorescences having bright yellow ray florets compared to the light pink-colored ray florets of plants of the cultivar Fiji. Other new cultivars have also been discovered and selected by the inventor as spontaneous mutations of the commercial cultivar Fiji. These include, but are not limited to, 'Dark Fiji' (disclosed in U.S. Plant Patent application Ser. No. 08/648,928) with lavender pink-colored ray florets and 'White Fiji' (disclosed in U.S. Plant Patent application Ser. No. 08/649,955) with pure white-colored ray florets.

Asexual reproduction of the new cultivar by terminal cuttings taken at Havant, Hampshire, United Kingdom, has shown that the unique features of this new Chrysanthemum are stable and reproduced true to type in successive generations.

The following traits have been repeatedly observed and are determined to be the unique characteristics of Bright Yellow Fiji. These characteristics in combination distinguish Bright Yellow Fiji as a new and distinct cultivar:

1. Flat capitulum form.
2. Decorative-type inflorescences.
3. Can be produced as a spray or standard cut Chrysanthemum.
4. Flowers after exposure to about eight weeks of short days.
5. Bright yellow ray florets.
6. Numerous inflorescences per plant when grown as a spray.
7. Numerous ray florets per inflorescence.
8. Strong and long peduncles.
9. Strong stems.

The cultivar Bright Yellow Fiji has not been observed under all possible environmental conditions. The phenotype may vary somewhat with variations in environment such as temperature, daylength and light intensity, without, however, any variance in genotype.

Plants of the new Chrysanthemum are similar to the cultivar Golden Polaris (not patented). However, in side-by-side comparisons conducted in Oxnard, Calif., under commercial practice, plants of the new Chrysanthemum differed from plants of the cultivar Golden Polaris in the following characteristics:

1. Plants of the new Chrysanthemum have shorter leaves than plants of the cultivar Golden Polaris.
2. Plants of the new Chrysanthemum have larger and taller inflorescences than plants of the cultivar Golden Polaris.
3. Ray florets of plants of the new Chrysanthemum are broader and more cupped than ray florets of plants of the cultivar Golden Polaris.

The accompanying colored photograph illustrates the overall appearance of the new cultivar, showing the colors as true as it is reasonably possible to obtain in colored reproductions of this type. The photograph comprises a side perspective view of a typical flowering stem of Bright Yellow Fiji grown as a spray (terminal inflorescence removed). The ray floret color in the photograph appears darker than the actual color due to light reflectance.

In the following description, color references are made to The Royal Horticultural Society Colour Chart except where general terms of ordinary dictionary significance are used. The following observations and measurements describe plants grown in Oxnard, Calif. under commercial practice in a glass-covered greenhouse with average night temperatures of 18 C., average day temperatures of 24 C., and light levels ranging from 2,000 (cloudy conditions) to 8,000 (sunny conditions) footcandles.

After sticking unrooted cuttings of the new cultivar in early Janurary, plants received 14 long day/short nights followed by short day/long nights until flowering in mid-March. Immature terminal inflorescences were removed and flowering stems were grown as sprays. Measurements and numerical values represent ranges or averages for six typical flowering stems.

Botanical classification: *Dendranthema grandiflora* cultivar Bright Yellow Fiji.

Commercial classification: Decorative cut chrysanthemum.

Parentage: Spontaneous mutation of the cultivar Fiji (U.S. Plant Patent application Ser. No. 08/648,930).

Propagation:

*Type.*—Terminal tip cuttings.

*Time to rooting.*—7 to 10 days with soil temperatures of 22 C.

*Rooting habit.*—Fine, fibrous and well-branched.

Plant description:

*Appearance.*—Perennial herbaceous decorative-type cut flower. Stems upright, uniform habit and freely branching. Can be grown as a spray (center bud removed) or as a standard (lateral buds removed). Flowering stem length about 85 cm.

*Vigor.*—Moderate.

*Foliage description.*—Leaf arrangement: Alternate. Leaf size, fully expanded: Length: 8.5 to 9.5 cm. Width: 5 to 5.5 cm. Leaf apex: Acuminate. Leaf base: Attenuate. Leaf margin: Palmately lobed. Leaf texture: Upper and under surfaces slightly pubescent. Veins prominent on under surface. Petiole length: 1.5 to 2 cm. Color: Young foliage upper surface: 147A. Young foliage under surface: 147B. Mature foliage upper surface: 147A. Mature foliage under surface: 147B. Venation upper surface: 147B. Venation under surface: 147B. Petiole: 147A.

Flowering description:

*Appearance.*—Decorative inflorescence form. Inflorescences borne on terminals above foliage. Florets arranged acropetally on a flat capitulum. Can be grown as a spray or as a standard.

*Flowering response.*—Under natural conditions, plants flower in the autumn/winter in the Northern Hemisphere. At other times of the year, inflorescence initiation and development can be induced under short day/long night conditions (at least 13.5 hours of darkness). Plants exposed to about 2 weeks of long day/short night conditions after planting followed by photoinductive short day/long night conditions, flower about 54 days later.

*Quantity of inflorescences.*—10 to 12 inflorescences per flowering stem.

*Bud.*—Size, showing color: Length: About 1 cm. Width: About 1.2 cm. Color: 5A.

*Inflorescence size.*—Diameter: 7.5 to 8 cm. Depth (height): 1.5 to 1.7 cm.

*Ray florets.*—Shape: Elongated. Size: Length: 3.4 to 3.8 cm. Width: 1.3 to 1.5 cm. Apex: Dentate. Base: Acute. Margin: Entire. Texture: Satiny, smooth, glabrous, ribbed lengthwise. Aspect: Cupped. Number of ray florets per inflorescence: About 285. Color: When opening, upper surface: 5A. When opening, under surface: 5A. Mature, upper surface: 5B, color does not fade with further development. Mature, under surface: 5D, color does not fade with further development.

*Disc florets.*—Shape: Tubular. Size: Length: About 2 mm. Width: About 1 mm. Number of disc florets per inflorescence: About 9. Color: Immature: 154A. Mature: 12A.

*Peduncle.*—Aspect: Strong. Length: First peduncle: 11 to 13 cm. Fourth peduncle: 14.5 to 16.5 cm. Texture: Glabrous. Color: 137B.

*Reproductive organs.*—Androecium: Present on disc florets only. Anther color: 12A. Pollen: Moderate, 12A in color. Gynoecium: Present on both ray and disc florets. Style color: 154A.

Disease resistance: No known Chrysanthemum diseases observed to date on plants grown under commercial greenhouse conditions.

Seed production: Seed production has not been observed.

It is claimed:

1. A new and distinct cultivar of Chrysanthemum plant named Bright Yellow Fiji, as illustrated and described.

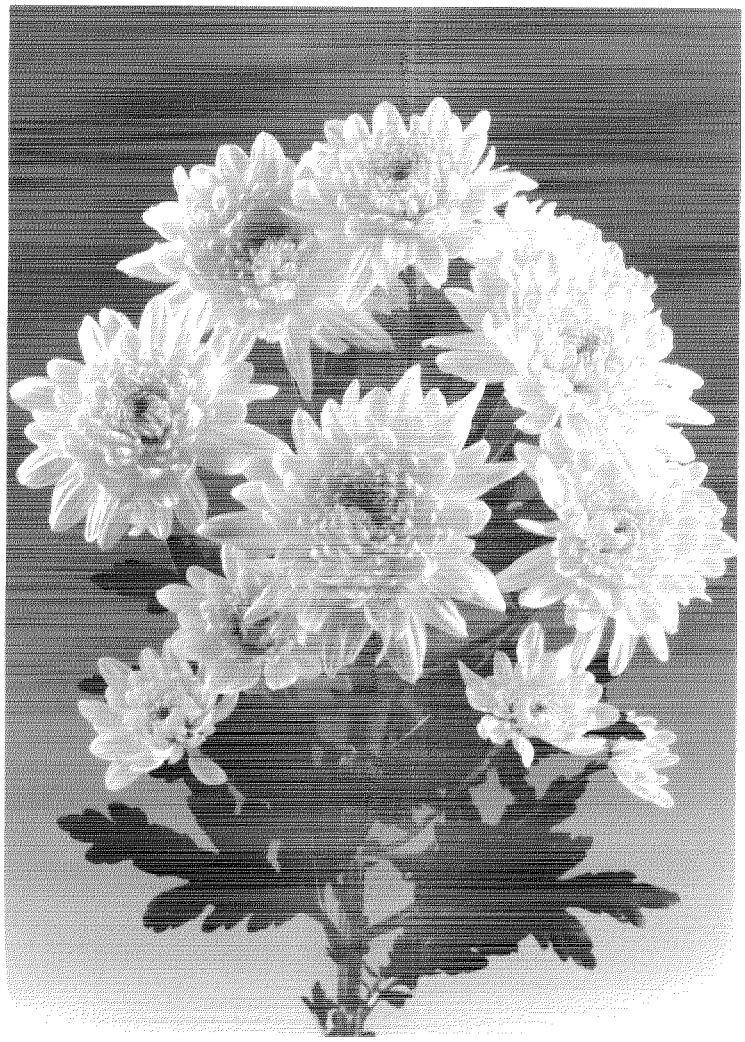

* * * * *